United States Patent [19]

Dörner

[11] Patent Number: 5,744,624
[45] Date of Patent: Apr. 28, 1998

[54] METHOD OF MAKING VITAMIN K1

[75] Inventor: Manfred Dörner, Florence, S.C.

[73] Assignee: Roche Vitamins Inc., Paramus, N.J.

[21] Appl. No.: 764,289

[22] Filed: Dec. 12, 1996

[30] Foreign Application Priority Data

Dec. 20, 1995 [CH] Switzerland ............ 3596/95

[51] Int. Cl.$^6$ .................................................. C07C 50/14
[52] U.S. Cl. ................................................. 552/299
[58] Field of Search ............................................. 552/299

[56] References Cited

U.S. PATENT DOCUMENTS

| | | | |
|---|---|---|---|
| 1,984,511 | 12/1934 | Anderson et al. | 260/56 |
| 2,376,984 | 5/1945 | Tishler | 260/396 |
| 3,076,004 | 1/1963 | Hirschmann | 260/410.5 |
| 3,948,958 | 4/1976 | Rapoport et al. | 260/396 |
| 4,906,411 | 3/1990 | Shinnaka et al. | 552/299 |
| 5,075,463 | 12/1991 | Kuo et al. | 552/299 |

FOREIGN PATENT DOCUMENTS

| | | |
|---|---|---|
| 8 321 690 | 6/1984 | Australia . |
| 1 054 085 | 5/1956 | Germany . |
| 76854 | 10/1973 | Japan . |
| 212 142 | 12/1982 | Japan . |
| 320 582 | 6/1964 | Switzerland . |

OTHER PUBLICATIONS

Fieser, L.F., and Cason, J., *J.A.C.S.*, 61:2559–2561 (1939).
Fieser, L.F., and Cason, J., *J.A.C.S.*, 61:3467 & 3471 (1939).
Fieser, L.F., and Cason, J., *J.A.C.S.*, 62:432–436 (1940).
Fieser, L.F., *J. Biol. Chem.*, 133:391–396 (1940).
Houben–Weyl, *Methoden der organischen Chemie*, vol. VII/3a:27–52 (1977).
Isler, O., and Doebel, K., *Helv. Chim. Acta*, 37:225 and 230 (1954).
Jackman, L.M., et al., *Helv. Chim. Acta*, 48:1332&1346 (1965).
Jacob III, P., et al., *J. Org. Chem.*, 41:3627–3629 (1976).
Karrer, P., et al., *Helv. Chim. Acta*, 27:317–319 (1944).
Mayer, H., et al., *Helv. Chim. Acta*, 47:221 & 226 (1964).
Morita, E., et al., Chemical Abstracts, 80(9):Abstract No. 48207 (1974).
Rüttimann, A., *CHIMIA*, 40(9):290–306 (1986).
Schmid, R., et al., *Helv. Chim. Acta*, 73:1276–1299 (1990).
Woods, et al., *Can. J. Chem.*, 35:941–943 (1957).

*Primary Examiner*—Jose G. Dees
*Assistant Examiner*—Barbara Badio
*Attorney, Agent, or Firm*—George W. Johnston; Dennis P. Tramaloni; Joseph P. Kirk, Jr.

[57] ABSTRACT

A process for the preparation of vitamin $K_1$ by the oxidation of an alkali metal salt of dihydrovitamin $K_1$ with hydrogen peroxide in the presence of an iron (III) salt at a pH of 13.7 to 14.3. The dihydrovitamin $K_1$ alkali metal salt is produced by the saponification of a dihydrovitamin $K_1$ diester with sodium hydroxide or potassium hydroxide. Conveniently, the oxidation process follows the saponification of dihydrovitamin $K_1$ without isolation of the product of the saponification reaction.

20 Claims, No Drawings

METHOD OF MAKING VITAMIN K1

BACKGROUND OF THE INVENTION

The present invention is concerned with a process for the manufacture of vitamin $K_1$ by oxidation of a dihydrovitamin $K_1$ alkali metal salt.

According to the relevant state of the art, which has been reviewed in Houben-Weyl, *Methoden der organischen Chemie*, Vol. VII/3a, 1977, pages 39 et seq., hydroquinone, alkyl-substituted hydroquinones, 1,4-dihydroxynaphthalene as well as alkyl-substituted naphthalenes can be oxidized very readily to the corresponding 1,4-quinones, with almost all known oxidizing agents being more or less usable. In general, the choice of the oxidizing agent depends on the stability of the quinone to be manufactured, with silver(I) oxide in diethyl ether or benzene in the presence of a mild drying agent, for example, sodium sulfate, being the reagent of choice for the manufacture of particularly sensitive quinones. Other frequently used oxidizing agents are, for example, iron(III) chloride in water or aqueous ethanol, sodium chlorate or potassium bromate in dilute sulphuric acid, chromium(VI) oxide in sulphuric acid or acetic acid, manganese(IV) oxide in dilute sulphuric acid, potassium nitrosodisulphonate and thallium(III) trifluoroacetate. Some of these oxidation methods are also used in the manufacture of vitamin $K_1$ and are accordingly of great practical significance; heretofore, for example, dihydrovitamin $K_1$ monoacetate has been saponified and subsequently oxidized to vitamin $K_1$ with silver oxide or iron oxide.

The conversion of non-esterified dihydrovitamin $K_1$ into vitamin $K_1$ with silver oxide is described especially in the papers of L. F. Fieser (et al.) in *J.A.C.S.* 61 (1939), 2559 et seq., 3467 and 3471, ibid. 62 (1940), 430 et seq. and *J. Biol. Chem.* 133 (1940), 391 et seq.; Isler et al., *Helv. Chim. Acta* 37 (1954), 225 and 230; Karrer et al., *Helv. Chim. Acta* 27 (1944), 317 et seq.; Woods et al., *Can. J. Chem.* 35 (1957), 941 et seq.; Mayer et al., *Helv. Chim. Acta* 47 (1964), 221 and 226; and Jackman et al., *Helv. Chim. Acta* 48 (1965), 1332 and 1346. According to Jacob et al., *J. Org. Chem.* 41 (1976), 3627 et seq., and more recent reports, for example, *Helv. Chim. Acta* 73 (1990), 1276–1299 (see pages 1280, 1283 and 1297) and *CHIMIA* 40 (1986), No. 9, 290–306 (see pages 300–302). Vitamin $K_1$ can also be produced by the oxidative demethylation of the dimethyl ether of dihydrovitamin $K_1$ using diammoniumcerium(IV) hexanitrate as the catalyst in a mixture of benzene or acetic acid, acetonitrile and water which functions as the solvent. A further method for the production of vitamin $K_1$ comprises saponifying dihydrovitamin $K_1$ monoacetate or monobenzoate with an alkali metal hydroxide and subsequently oxidizing with air [Jackman et al., *Helv. Chim. Acta* 48 (1965), 1332; Swiss Patent 320 582; and Isler et al., *Helv. Chim. Acta* 37 (1954), 225]. A diester, especially the diacetate, can also be used as the starting material in place of a monoester, this being briefly mentioned in Japanese Patent Publication (Kokai) 212 142/1982. Oxidation with air has been and is still being used as the last step of many large scale processes for the manufacture of vitamin $K_1$. However, such processes have the serious disadvantage that the troublesome byproduct vitamin $K_1$ epoxide also results in a considerable amount.

Further methods for the oxidation of dihydrovitamin $K_1$ to vitamin $K_1$, and their disadvantages, are briefly referred to in Japanese Patent Publication (Kokai) 76854/1973, namely the inefficient, environmentally unfriendly and expensive oxidations with silver oxide, lead oxide, manganese dioxide, nickel peroxide and dimethyl sulphoxide. The invention which forms the object of said Japanese patent publication comprises converting dihydrovitamin $K_1$ into vitamin $K_1$ using hydrogen peroxide (in aqueous solution) as the oxidizing agent and optionally in an organic solvent, for example, hexane, heptane, diethyl ether, diisopropyl ether, petroleum ether, petroleum benzene, ligroin, isopropanol, dioxan, benzene, toluene etc.

SUMMARY OF THE INVENTION

The object of the present invention is the manufacture of vitamin $K_1$ starting from the hitherto used dihydrovitamin $K_1$ monoacetate monobenzoate (hereinafter "dihydrovitamin $K_1$ acetate benzoate") or an analogous diester (monoalkanoylate monoaroylate) while minimizing the aforementioned disadvantages of the state of the art (especially by reducing the solvent-carrying exhaust air and reducing the content of vitamin $K_1$ epoxide) and simultaneously obtaining yields which are as high as possible. This object is achieved in accordance with the invention by saponifying the dihydrovitamin $K_1$ diester with an alkali metal hydroxide to the corresponding dihydrovitamin $K_1$ alkali metal salt, then oxidizing this to vitamin $K_1$ with hydrogen peroxide, instead of air, in the presence of an iron(III) salt, especially of iron(III) sulfate or iron(III) chloride, at a pH in the region of about 14.

DETAILED DESCRIPTION OF THE INVENTION

The process of the present invention is an oxidation process for the manufacture of vitamin $K_1$ (I), comprising oxidizing an alkali metal salt of dihydrovitamin $K_1$ with hydrogen peroxide in the presence of an iron(III) salt and at a pH of about 13.7 to about 14.3. A further aspect of the present invention comprises producing the dihydrovitamin $K_1$ alkali metal salt used in the oxidation process in accordance with the invention, especially the sodium or potassium salt, by saponifying a dihydrovitamin $K_1$ diester of the formula

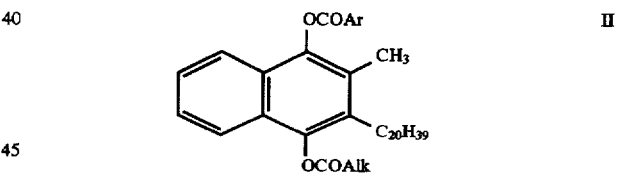

wherein Ar signifies an aryl group, Alk signifies a lower alkyl group and $C_{20}H_{39}$ signifies the 3,7,11,15-tetramethylhexadec-2-enyl group, with sodium hydroxide or potassium hydroxide.

In this definition it is understood that the term "aryl group" (Ar) refers in general to a phenyl or naphthyl group, which in each case can be optionally substituted, with the optionally present substituents being selected especially from lower alkyl groups, lower alkoxy groups and halogen atoms. However, Ar preferably signifies unsubstituted phenyl. The term "lower alkyl group" or Alk denotes especially a $C_{1-4}$ alkyl group, which applies not only to Alk but also to the aforementioned lower alkyl groups as substituents. The aforementioned lower alkoxy groups also contain especially 1 to 4 carbon atoms. "Halogen atoms" refer to fluorine, chlorine, bromine and iodine. Preferably, Alk signifies methyl. Accordingly, formula II preferably represents dihydrovitamin $K_1$ acetate benzoate. However, other diesters of formula II, as defined in more detail on the basis of the foregoing explanation, can be used in the process in accordance with the invention.

Conveniently, the oxidation process in accordance with the present invention includes the saponification of the dihydrovitamin $K_1$ diester without firstly isolating the saponification product (dihydrovitamin $K_1$ sodium salt or potassium salt). On practical grounds this two-stage process can be carried out as follows:

The dihydrovitamin $K_1$ diester of formula II is saponified with an excess of sodium hydroxide or potassium hydroxide in a two-phase aqueous-organic solvent mixture. This solvent mixture conveniently consists of an aqueous-alcoholic phase and an organic phase which is not significantly miscible therewith or not significantly soluble therein. Each phase may be pre-treated with a clarifying agent, for example, an aqueous solution of sodium dithionite. After carrying out the saponification, which can be conveniently performed while stirring at room temperature or a temperature which is not substantially higher, the thus-produced dihydrovitamin $K_1$ alkali metal salt is present for the most part in the aqueous-alcoholic phase. This phase, after its separation from the organic phase, may, if desired, be washed with fresh organic solvent (conveniently of the same type). In this case also, the organic solvent can be pre-treated with a clarifying agent. Instead of discarding the organic phase and rinsings, for economical efficiency, the solvent can be recovered therefrom, for example by distillation, and recycled. Then, further organic solvent, again optionally pre-clarified, is added to the separated aqueous-alcoholic solution containing the alkali metal salt and the resulting two-phase mixture is treated with sufficient acid, until a pH of the aqueous-alcoholic phase of about 14 (in the region of about 13.7 to about 14.3) has been achieved. The acid may be any mineral or organic acid, for example aqueous hydrochloric or sulfuric acid, or formic or acetic acid, and is preferably acetic acid. Subsequently, the batch is treated with an aqueous solution of the iron(III) salt and then with an aqueous solution of hydrogen peroxide. In both cases the treatment is suitably effected while stirring at room temperature or a temperature which is not substantially higher, for example about 40° C. In this manner the oxidation of the dihydrovitamin $K_1$ alkali metal salt with hydrogen peroxide, catalyzed by the iron(III) salt, to vitamin $K_1$ is effected. The product collects in the organic phase in a relatively short time, since the oxidation normally takes only a few minutes. The end of the oxidation is normally readily recognized by a color change, roughly from brown to yellow, and, moreover, by the observation that oxygen continuously evolves from the reaction mixture. For the working up and isolation of the vitamin $K_1$ from the organic phase, the organic phase is initially separated. It can then be washed with water, which is optionally supplemented with acetic acid, and dried over a drying agent, for example, anhydrous sodium sulfate, and if necessary treated with a decolorizing agent, for example, active charcoal or aluminum oxide, and thereafter filtered, and concentrated under reduced pressure. The resulting vitamin $K_1$ precipitate can then be isolated conveniently by filtration from the concentrate which, if necessary, has previously been deodorized with steam. The vitamin $K_1$ manufactured and isolated in this manner has a very good quality, since it contains very little vitamin $K_1$ epoxide byproduct and normally has a purity of more than 98%. In addition, the yield, based on the vitamin $K_1$ diester starting material, is generally more than about 85%.

With respect to the oxidation process in accordance with the invention, for the manufacture of one part by weight of the vitamin $K_1$ end product there is conveniently used about 0.005 to about 0.01 part by weight of the iron(III) salt used as the catalyst [for example, $Fe_2(SO_4)_3$; in practice, however, having regard to its ready availability iron(III) sulfate pentahydrate is preferably used in this case to produce the aqueous solution and accordingly the conveniently used proportional amount of this pentahydrate based on the amount of vitamin $K_1$ is correspondingly higher].

Alternatively, based on the amount of dihydrovitamin $K_1$ diester (for example, acetate benzoate) used in the pre-step (saponification) there is conveniently used about 0.002 to about 0.01 equivalent of iron(III) salt per equivalent of diester, preferably about 0.005 to about 0.007 equivalent of iron(III) salt (in the case of the acetate benzoate and iron(III) sulfate these ranges correspond to about 0.001 to about 0.01 part by weight of iron(III) sulfate per part by weight of acetate benzoate or about 0.003 to about 0.004 part by weight, respectively). The aqueous hydrogen peroxide solution which is used conveniently has a concentration of about 30 weight percent (wt. %) to about 40 wt. %, preferably a concentration of about 35 wt. %. Based on the amount of dihydrovitamin $K_1$ diester used in the saponification there is conveniently used in the case of dihydrovitamin $K_1$ acetate benzoate about 0.2 to about 0.6 part by weight, preferably about 0.3 to about 0.35 part by weight, of aqueous hydrogen peroxide solution, for example 35% aqueous hydrogen peroxide solution, per part by weight of diester. Viewed differently, namely as equivalents, about 1.5 to about 2.5 equivalents of hydrogen peroxide as such ($H_2O_2$), preferably about 1.85 to about 2.13 equivalents, are conveniently used per equivalent of diester. Based on the amount of the finally manufactured vitamin $K_1$ there is conveniently used per part by weight of this product about 0.3 to about 0.8 part by weight of aqueous hydrogen peroxide solution (35% as an example), preferably about 0.45 to about 0.53 part by weight. Again viewed differently, there are conveniently used per equivalent of the finally manufactured vitamin $K_1$ about 1.8 to about 2.8 equivalents of hydrogen peroxide as such ($H_2O_2$), preferably about 2.1 to about 2.4 equivalents.

As mentioned earlier, the oxidation process in accordance with the invention is conveniently carried out in a two-phase aqueous-organic solvent mixture which consists on the one hand of an aqueous-alcoholic phase and on the other hand of an organic phase. In general, a $C_{1-3}$-alkanol, i.e. methanol, ethanol, n-propanol or isopropanol, is suitable as the alcohol. However, methanol is preferably used. The organic phase is suitably an aliphatic hydrocarbon, for example, hexane, heptane or a mixture of hydrocarbons, for example petroleum ether; a halogenated hydrocarbon, for example, methylene chloride; an aromatic hydrocarbon, for example, benzene or toluene; or benzine or a fraction thereof, for example, ligroin. Petroleum ether is preferably used as the organic phase.

The alcohol:water volume ratio in the aqueous-alcoholic phase is conveniently about 3:1 to about 7:1. When the preferred alcohol methanol is used, this volume ratio is generally about 3:1 to about 7:1, preferably about 4:1 to about 6:1. With respect to the two-phase solvent mixture, the volume ratio aqueous-alcoholic phase:organic phase is generally about 3:2 to about 2:3, preferably about 10:8 to about 1:1. For each gram of dihydrovitamin $K_1$ alkali metal salt, or for each equivalent of dihydrovitamin alkali metal salt, (for example potassium salt) to be oxidized, there is conveniently used about 0.001 to about 0.01 liter or about 10 to about 25 liters, respectively, of two-phase solvent mixture, preferably about 0.002 to about 0.006 liter or about 15 to about 20 liters, respectively.

The oxidation is conveniently carried out at temperatures in the range of about 15° C. to about 40° C., preferably at room temperature.

With respect to the saponification which precedes the oxidation process in accordance with the invention, there are conveniently used per equivalent of dihydrovitamin $K_1$ diester of formula II about 22 to 30 equivalents of sodium hydroxide or potassium hydroxide, preferably about 25 to about 27 equivalents of this base. Potassium hydroxide is preferably used as the base. The concentration of the aqueous sodium hydroxide or potassium hydroxide solution which is used is conveniently about 40 weight percent (wt. %) to about 60 wt. %, preferably about 55 to about 58 wt. %. As mentioned earlier, the saponification is also conveniently carried out in a two-phase aqueous-organic solvent mixture which consists on the one hand of an aqueous-alcoholic phase and on the other hand of an organic phase. The respective information given earlier with respect to the nature and the relative volume ratios of the components of this solvent mixture in relation to the oxidation process also apply in essence to the saponification. In the saponification there is conveniently used for each gram of dihydrovitamin $K_1$ diester of formula II, or for each equivalent of dihydrovitamin $K_1$ diester of formula II (for example the acetate benzoate) to be saponified about 0.01 to about 0.05 liter or about 10 to about 25 liters , respectively, of two-phase solvent mixture, preferably about 0.02 to about 0.04 liter or about 15 to about 20 liters, respectively. The saponification is conveniently carried out at temperatures in the range of about 15° C. to about 30° C., preferably at room temperature, and as a rule takes one to three hours, especially about 2 hours.

The clarification, for example, using an aqueous sodium dithionite solution, optionally used not only in the saponification but also in the subsequent oxidation, serves to lighten and clarify the reaction mixture which tends to darken during the respective reaction, thus making the particular reaction easier to follow optically. Moreover, it has been found that the finally obtained vitamin $K_1$ has a better quality when the clarifying agent is used.

The present invention is illustrated by the following Examples:

EXAMPLE 1

75 g (0.261 mol) of potassium hydroxide are dissolved in 55.5 ml of water under nitrogen in a 1.5 l four-necked sulphonation flask equipped with a thermometer, condenser, dropping funnel and stirrer. 329.5 ml of methanol are added to the solution, upon which an exothermic reaction takes place. The aqueous-methanolic solution is cooled to 10° C. within 10 minutes. A solution of 0.5 g of sodium dithionite in 7.5 ml of water is then added and the mixture is heated to 20° C. in a water bath.

A solution of 30 g (0.05 mol) of dihydrovitamin $K_1$ acetate benzoate in 550 ml of high-boiling petroleum ether, previously treated with 20 ml of 10% aqueous sodium dithionite solution, is subsequently added dropwise within 5 minutes, while stirring, to the above mixture at 20°–25° C. and the resulting mixture is stirred vigorously at 20°–24° C. for 2 hours. If the reaction solution becomes brown in color during the stirring, it is rapidly clarified with the additional of sufficient 10% sodium dithionite solution. The mixture is then left to stand for a sufficient time for the phases to separate and thereafter the upper petroleum ether phase is removed under pressure using a glass tube and nitrogen and the lower methanolic phase is washed with four 195 ml aliquots of high-boiling petroleum ether which have been previously treated with 10% aqueous sodium dithionite solution. During this washing procedure the methanolic solution should remain yellow and, accordingly, any subsequently darkened solution is immediately clarified with the addition of sufficient 10% aqueous sodium dithionite solution. The petroleum ether extracts are discarded. In this manner (saponification) there is obtained a yellow methanolic solution of dihydrovitamin $K_1$ potassium salt.

500 ml of high-boiling petroleum ether, previously treated with 20 ml of 10% aqueous sodium dithionite solution, are added to the yellow solution of the previous step. While stirring vigorously about 50–52 ml of glacial acetic acid are added dropwise, the last 5–7 ml particularly slowly. Since the reaction is exothermic, this addition is effected while cooling with an ice bath at 10° C. in order that the reaction temperature does not exceed 30° C. Moreover, should the reaction solution darken, it can be clarified by the addition of 10% aqueous sodium dithionite solution. When the solution is yellow with a green cast, which occurs at pH 14, the addition of glacial acetic acid is stopped.

175 mg of iron(III) sulfate pentahydrate are dissolved in 7.5 ml of water and the solution is added to the reaction mixture of the previous step while stirring, whereupon the mixture becomes olive green in color (in this reaction step sodium dithionite solution is no longer added). Then, 7.9 ml of aqueous hydrogen peroxide solution are added dropwise within 5 minutes, whereby the temperature of the reaction solution should not exceed 30° C. For this purpose, the exothermic reaction is held under control by cooling in an ice bath at 5°–10° C. (It is observed that at the beginning of the hydrogen peroxide addition the color of the reaction solution changes from olive green to dark brown and that oxygen continuously evolves from the solution. In the course of the oxidation the color again changes from dark brown via brown to yellow; it is golden yellow after completion of the oxidation.)

After completion of the reaction the solution is left to stand for a sufficient time for phase separation to occur. Then, the yellow petroleum ether phase is separated and washed in succession with 200 ml of dilute acetic acid (50 mg of glacial acetic acid in 200 ml of water) until the pH of the acetic acid phase is about 6–7 and twice with 200 ml of water each time. The petroleum ether phase is dried over 19 g of anhydrous sodium sulfate and subsequently filtered. 0.75 g of active charcoal is added to the solution and the mixture is stirred for 30 minutes, thereafter 10 g of alkali-free, neutral aluminum oxide containing 2% water (prepared from 9.8 g of aluminum oxide and 0.2 g of water by stirring at room temperature for 1 hour) are added and the solution is stirred for a further 30 minutes. After removing the solids by filtration under nitrogen the petroleum ether solution is concentrated at 60° C./40 mbar, likewise under nitrogen, in a brown glass flask in order to protect the material from light. Finally, the thus-produced yellowish, oily vitamin $K_1$ is filtered off under pressure.

EXAMPLE 2

A solution of about 1.4 kg of sodium dithionite in about 101 of water is added at room temperature to a solution of about 30 kg of dihydrovitamin $K_1$ acetate benzoate in about 550 l of petroleum ether under nitrogen. There is obtained a yellow solution which, upon darkening, is clarified by the addition of further sodium dithionite solution prior to the next step. A solution of about 75 kg of potassium hydroxide in about 56 kg of water and about 253 kg of ethanol is subsequently added to the solution and the mixture is stirred for about 2 hours.

The methanolic solution is separated and washed several times with petroleum ether, whereafter the methanolic solution is diluted with about 280 kg of petroleum ether and about 74 kg of methanol and, when required, clarified by the addition of aqueous sodium dithionite solution. The pH is adjusted to about 14 by the addition of about 52–60 kg of acetic acid and, if necessary, further sodium dithionite solution. A solution of about 0.15 kg of iron(III) sulfate in about 15 kg of water is added to the mixture, followed by 7–10 kg of about 35% aqueous hydrogen peroxide solution. The separated methanolic phase is extracted with petroleum ether and the petroleum ether phase is firstly washed with very dilute aqueous acetic acid solution and thereafter dried with anhydrous sodium sulfate which afterwards is separated. After decolorization of the petroleum ether phase with about 1 kg of active charcoal and about 10 kg of aluminum oxide the decolorizing agents are separated by filtration and washed with petroleum ether. The combined petroleum ether filtrates are then concentrated under reduced pressure. The residue is deodorized with steam and the vitamin $K_1$ precipitate is filtered off. In this manner there is obtained an about 80–92% yield of vitamin $K_1$.

EXAMPLE 3

Summary:

Dihydrovitamin $K_1$ acetate benzoate is dissolved in petroleum ether and the solution is decolorized with aqueous sodium dithionite solution. It is subsequently saponified with an aqueous-methanolic potassium hydroxide solution for 2 hours and the methanolic phase is extracted with petroleum ether and, if necessary, again decolorized. After diluting the petroleum ether phase with further petroleum ether and methanol it is adjusted to pH 14 by adding glacial acetic acid. It is then oxidized with hydrogen peroxide in the presence of iron(III) sulfate as the catalyst at below 30° C. The petroleum ether phase is washed with water, dried with anhydrous sodium sulfate and decolorized with active charcoal together with aluminum oxide. The filtrate is concentrated under reduced pressure and purified by steam distillation. Finally, the thus-obtained vitamin $K_1$ is filtered off.

(i) Saponification 75 kg of potassium hydroxide are added under nitrogen to a mixture, cooled to 20°+1° C., of 56 l of water and 320 l (253 kg) of methanol, with the temperature rising to 40°–50° C. The mixture is stirred at this temperature until the potassium hydroxide has dissolved completely (45–60 minutes) and then the solution ["(a)"] is cooled to 15°–25° C.

30 kg of crude dihydrovitamin $K_1$ acetate benzoate are dissolved in 500 l (335 kg) of high-boiling petroleum ether while stirring under nitrogen in a stirring vessel. Then, the contents of the vessel and 50 l (35 kg) of petroleum ether rinsings [together "solution (b)"] are introduced with nitrogen via lower outlets into a further vessel into which solution (a) is subsequently also conducted. A solution of 1.4 kg of sodium dithionite in 10 l of water is added to the mixture of solutions (a) and (b) for the purpose of clarification and then this entire saponification solution ["(c)"] is stirred at 20°–25° C. for 120–125 minutes. During the stirring period the color of the saponification solution is continuously controlled: should the color deviate from yellow (become darker), the solution must be clarified by the addition of further aqueous sodium dithionite solution (0.3 kg/5 l). After completion of the saponification, solution (c) is left to stand for 20 to a maximum of 30 minutes.

(ii) Extraction Prior to Oxidation 640 l (429 kg) of high-boiling petroleum ether are treated with a solution of 0.3 kg of sodium dithionite in 5 l of water in a stirring vessel. After separation of the aqueous phase the petroleum ether phase ["(d)"] remains.

The lower methanolic phase of solution (c) is added to 160 l (107 kg) of petroleum ether phase (d) in a stirring vessel for the purpose of extraction and, after separation of the petroleum ether phase, the lower methanolic phase is again extracted with 160 l (107 kg) of petroleum ether phase (d). This two-fold extraction of the methanolic phase is repeated once more. Methanolic phase [(e)] remains after separation of the petroleum ether phase.

560 l (429 kg) of high-boiling petroleum ether are treated with a solution of 0.3 kg of sodium dithionite in 5 l of water in a stirring vessel. Petroleum ether phase [(f)] remains after separation of the aqueous phase.

Methanolic phase (e) is added to 100 l (67 kg) of petroleum ether phase (f) in a stirring vessel in order to repeat the extraction and, after separating the petroleum ether phase, there remains methanolic phase [(g)] which consists of a methanolic solution of dihydrovitamin $K_1$ potassium salt.

(iii) Preparation for Oxidation 0.5 kg of sodium dithionite is added to 10 l of water while stirring, a further 3 l of water are then added and the mixture is stirred for 5 minutes [solution (h)].

In a separate vessel 0.15 kg of iron(III) sulfate hydrate is added to 7 l of water while stirring, a further 3 l of water are added and the mixture is stirred for 5 minutes (iron sulfate solution).

200 l (134 kg) of high-boiling petroleum ether are introduced into an oxidation vessel and methanolic phase (g) is added to this petroleum ether. A mixture of 174 kg (260 l) of high-boiling petroleum ether and 74 kg (94 l) of methanol is then added. If the contents of the oxidation vessel are not lemon-yellow, a further 1–5 l (1.1–5.4 kg) of aqueous sodium dithionite solution is added while stirring until the color changes from brown to lemon-yellow.

53–57 l (52–60 kg) of glacial acetic acid are slowly dosed at a temperature below 30° C. into the oxidation vessel until a pH value of 14 has been attained. If the solution is no longer lemon-yellow, a further 0.1–5 l (0.1–5.4 kg) of aqueous sodium dithionite solution are slowly added.

The iron sulfate solution is then added to the solution in the oxidation vessel, followed by 5 l of water rinsings.

(iv) Oxidation

7–8.5 l (7.7–9.6 kg) of 35% aqueous hydrogen peroxide solution are dosed into the mixture in the oxidation vessel within 4–6 minutes at 27°–30° C. In the course of the resulting oxidation the color changes firstly from olive green to dark brown; thereafter the mixture clarifies, becoming darker for a short time and then immediately changing to yellow. As soon as the mixture has become yellow in color, the hydrogen peroxide addition is interrupted.

(v) Extraction After Oxidation

After oxidation and phase separation have been carried out the lower methanol phase is transferred into a stirring vessel already containing 150 l (100 kg) of petroleum ether. After extraction the additional methanolic phase is removed. Petroleum ether phase [(i)] remains.

The petroleum ether phase which is still in the oxidation vessel is washed with 200 l of water and, after the addition of 0.5–0.8 l (0.52–0.84 kg) of glacial acetic acid, extracted at pH 3.6–4.0. The separated petroleum ether phase together with rinsings is then transferred with 100 l (67 kg) of high-boiling petroleum ether into a washing vessel and washed therein with 200 l of water. After separation of the lower aqueous phase this is extracted in a further vessel with 100 l (67 kg) of high-boiling petroleum ether and its pH is measured. Should it be greater than 6, the petroleum ether phase contained in the washing vessel is again washed with 200 l of water and the lower aqueous phase is separated and its pH is measured. This procedure is repeated until the measured pH of the aqueous phase is less than 6, possibly four times. The petroleum ether phase washed in this manner consists almost exclusively of vitamin $K_1$ and solvent.

(vi) Working up of The Petroleum Ether Phase 30 l of the petroleum ether solution contained in the washing vessel are transferred into a further vessel, the remainder (majority) of the petroleum ether solution is transferred into a stirring vessel and the 30 l of petroleum ether solution are returned to the washing vessel for extraction therein with an acetic acid solution consisting of 100 l of water and 50 ml (0.053 kg) of glacial acetic acid. The lower aqueous phase of this extraction is separated and its pH value is measured (nominal value: 4–5). The petroleum ether solution in the washing vessel is then extracted with 100 l of water and the pH of the separated lower aqueous phase is measured (nominal pH: 6–7). Finally, the petroleum ether solution remaining in the washing vessel is combined with that (the majority, (i)) in the stirring vessel.

(vii) Drying and Decolorizing 10 kg of anhydrous sodium sulfate are added to the petroleum ether solution in the stirring vessel. After stirring for 30 minutes and drying the drying agent is separated by filtration and the filtered petroleum ether solution together with likewise filtered petroleum ether rinsings (50 l) from the stirring vessel are returned to the stirring vessel. 1.0 kg of active charcoal is added to the petroleum ether solution under nitrogen and the mixture is stirred for 30 minutes. After the addition of 10 kg of alkali-free aluminum oxide deactivated with 200 ml of water the mixture is again stirred for 30 minutes. Then, the suspension and two petroleum ether rinsings (100 l each) are filtered.

The decolorization with active charcoal and aluminum oxide is repeated and a sample of the filtrate is tested for color and fluorescence. Depending on the result the procedure using active charcoal alone (for decolorization) or using aluminum oxide alone (for removing fluorescent components) is repeated until the petroleum ether solution has been decolorized.

(viii) Evaporation of The Petroleum Ether Solution Containing The Vitamin $K_1$

The decolorized petroleum ether solution is continuously evaporated under 200 mbar pressure at 85°–90° C. (steam outlet) and a throughput velocity of 120–130 l/h while stirring. The concentrated vitamin $K_1$ solution is then transferred into a vessel and stored under nitrogen at 0.3 bar pressure.

The evaporation and subsequent storage (under 0.3 bar nitrogen pressure) of the concentrated vitamin $K_1$ solution are repeated twice (1st repetition: 30–40 mbar, steam outlet 70°–80° C., throughput velocity 30–40 l/h; 2nd repetition: <25 mbar, steam outlet 55°–65° C., throughput velocity 80–110 l/h).

(ix) Deodorization With Steam

The contents of the last storage vessel are subjected to a steam distillation at less than 25 mbar and a mantle temperature of 68°–74° C. The collected vitamin $K_1$ is subsequently stored under nitrogen at 0.3 bar pressure.

(x) Fine Filtration and Packaging

Three batches of vitamin $K_1$ are filtered through a combination of three filters (2/10/0.2 mm) using a geared pump at a maximum pressure of 4 bar, collected and tested. If the analysis is unsatisfactory, the product is processed with two further batches in the same manner.

After mixing three batches the mixture is analyzed in order to verify the high quality.

After stirring under nitrogen for one hour the thus-obtained vitamin $K_1$ of good quality (purity) can be filled into cans and covered with nitrogen. The cans are subsequently sealed and labeled.

What is claimed is:

1. A process for the manufacture of vitamin $K_1$, comprising oxidizing an alkali metal salt of dihydrovitamin $K_1$ with hydrogen peroxide in the presence of an iron(III) salt at a pH of about 13.7 to about 14.3.

2. A process for the manufacture of vitamin $K_1$ comprising:

a) saponifying a dihydrovitamin $K_1$ diester of the formula

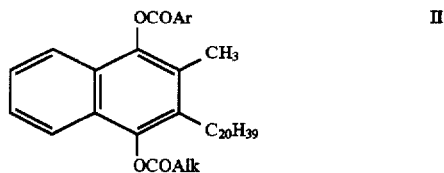

wherein Ar is an aryl group, Alk is an alkyl group and $C_{20}H_{39}$ is a 3,7,11,15-tetramethylhexadec-2-enyl group with an alkali metal hydroxide to produce a dihydrovitamin $K_1$ alkali metal salt; and b) oxidizing the dihydrovitamin $K_1$ alkali metal salt with hydrogen peroxide in the presence of an iron(III) salt at a pH of about 13.7 to about 14.3.

3. The process of claim 2 wherein the dihydrovitamin $K_1$ alkali metal salt produced in step (a) is not isolated prior to step (b).

4. The process of claim 2 wherein the dihydrovitamin $K_1$ diester is the acetate benzoate.

5. The process of claim 2 wherein step (a) takes place in a first two phase aqueous/organic solvent mixture and step (b) takes place in a second two phase aqueous/organic solvent mixture.

6. The process of claim 5 wherein the aqueous/organic-solvent mixtures of step (a) and step (b) comprise an aqueous-alcoholic phase and an organic phase which is not significantly miscible with or soluble in the aqueous-alcoholic phase.

7. The process of claim 6 wherein the alcohol of the aqueous-alcohol phase is selected from the group consisting of methanol, ethanol, n-propanol and isopropanol.

8. The process of claim 6 wherein the alcohol of the aqueous-alcoholic phase is methanol.

9. The process of claim 6 wherein the organic-solvent phase is petroleum ether.

10. The process of claim 2 wherein the iron(III) salt is selected from the group consisting of iron(III) sulfate and iron(III) chloride.

11. The process of claim 2 wherein the iron(III) salt is iron(III) sulfate.

12. The process of claim 2 wherein the pH of about 13.7 to about 14.3 in step (b) is obtained by the addition of a mineral acid.

13. The process of claim 2 wherein the pH of about 13.7 to about 14.3 in step (b) is obtained by the addition of an organic acid.

14. The process of claim 2 wherein the pH of about 13.7 to about 14.3 in step (b) is obtained by the addition of acetic acid.

15. The process of claim 2 wherein the aryl group is selected from the group consisting of phenyl and naphthyl each being unsubstituted or substituted with the substituents selected from $C_{1-4}$ alkyl groups, $C_{1-4}$ alkoxy groups, and fluorine, chlorine, bromine and iodine atoms.

16. The process of claim 2 wherein the aryl group is unsubstituted phenyl.

17. The process of claim 2 wherein the alkyl group is selected from the group consisting of $C_{1-4}$ alkyls.

18. The process of claim 2 wherein the alkyl group is methyl.

19. The process of claim 2 wherein the alkali metal hydroxide is selected from the group consisting of sodium hydroxide and potassium hydroxide.

20. A process for the manufacture of vitamin $K_1$ comprising:

a) saponifying dihydrovitamin $K_1$ acetate benzoate of the formula

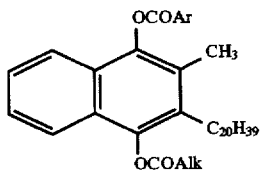   II wherein Ar is an unsubstituted phenyl, Alk is methyl and $C_{20}H_{39}$ is a 3,7,11,15-tetramethylhexadec-2-enyl group
with sodium hydroxide in a two phase solution wherein the sodium hydroxide is dissolved in a first phase of the two phase solution said first phase comprising an aqueous-methanolic solution and the dihydrovitamin $K_1$ acetate benzoate in a second phase of the two phase solution said second phase comprising petroleum ether and mixing the first and second phases together for sufficient time to allow the saponification reaction to occur to produce a dihydrovitamin $K_1$ alkali metal salt;

b) allowing the first and second phases to separate and removing the petroleum ether phase;

c) washing the remaining aqueous-methanolic phase with at least one petroleum ether wash;

d) adding a new petroleum ether phase to the remaining aqueous-methanolic phase and acidifying the mixture with sufficient acetic acid to obtain a pH of about 13.7 to about 14.3;

e) oxidizing the dihydrovitamin $K_1$ alkali metal salt by adding aqueous iron(III) sulfate solution and aqueous hydrogen peroxide solution sequentially to the mixture obtained in (d) while mixing and allowing sufficient time for the oxidation reaction to be completed;

f) allowing the petroleum ether and aqueous-methanolic phase to separate and removing the aqueous-methanolic phase;

g) washing the remaining petroleum ether phase with a dilute aqueous acetic acid solution and decolorizing the petroleum ether phase with activated charcoal and aluminum oxide and filtering the petroleum ether phase;

h) concentrating the petroleum ether filtrate and deodorizing the filtrate with steam; and i) filtering off the vitamin $K_1$.

* * * * *